United States Patent [19]

Mojonnier

[11] Patent Number: Plant 7,708

[45] Date of Patent: Nov. 12, 1991

[54] ALSTROEMERIA PLANT NAMED DIANA

[76] Inventor: Erwin Mojonnier, Encinitas, Calif.

[21] Appl. No.: 556,431

[22] Filed: Jul. 24, 1990

[51] Int. Cl.[5] ..... A01H 5/00
[52] U.S. Cl. ..... Plt./68
[58] Field of Search ..... Plt./68, 87.1

*Primary Examiner*—Howard J. Locker
*Attorney, Agent, or Firm*—Foley & Lardner

[57] ABSTRACT

An Alstroemeria plant named Diana, characterized by its flowers which are pink and red cheeks and have prominent markings on the upper petals and less prominent markings on the lower petal, and a yellow patch near the throat; few non-flowering stems per plant; winter production beginning in early December, and good post-harvest flower color retention.

1 Drawing Sheet

The present invention relates to a new and distinct cultivar of Alstroemeria plant hereinafter referred to by the cultivar name Diana.

Diana is a product of a planned breeding program which had the primary objectives of creating new Alstroemeria cultivars having unique flower color and being capable of early winter production with low maintenance requirements. The latter term refers to the production of a minimum of non-flowering stems. Such traits in combination were not present in previously available commercial cultivars.

In order to fully understand an important characteristic of the new cultivar, an explanation of typical current winter production schedules for cut flowers of Alstroemerias would be helpful. Standard industry growing practices normally utilize only natural daylight. As a result, late fall and winter production of Alstroemeria cut flowers, due to reduced levels of light during these periods, typically requires 12 weeks or more of growing time from the planting of the rhizome cutting to the initiation of flowering. Even more time is required for further flowering to produce a stem ready to sale. With certain varieties, the period of time from planting to flowering can extend up to almost six months. This time will substantially vary from variety to variety, and growing techniques and conditions also affect the growing period. For example, a larger cutting will obviously require a shorter growing time than a relatively small cutting. High temperatures normally have an adverse affect on growth, as does reduced light.

The commercial implications of relatively slow growth characteristics under natural light conditions should be obvious. Increased bench or field time (if grown outdoors where climates permit) substantially increases production costs, which in turn result in increased costs per stem due to the increased cost of production. Total production of Alstroemeria cut flowers during such period is also correspondingly less. This adversely affects the normal supply/demand ratio in the marketplace, and as a result cut flowers of Alstroemeria are substantially more costly during the winter months than during the periods beginning in March when production increases. It is not unusual for stem prices to be 50% higher during the winter months of December, January, and February.

The inventor has discovered that through photoperiodic growth practices, certain cultivars can be brought into flowering in the late fall and winter periods in substantially reduced periods of time, thereby increasing production during these periods. However, all cultivars are not adaptable to photoperiodic control.

Through extensive breeding, the inventor has been able to produce new Alstroemeria cultivars, of which Diana is one, specifically adaptable to photoperiodic control. The inventor's preferred growing technique includes growing the newly stuck plants under natural light conditions for approximately one month without light supplement. After approximately one month, the day length is effectively increased by providing four hours of artificial lighting by techniques or methods well known in the industry.

A preferred growing regimen which has provided excellent results comprises planting established rhizome divisions in ground beds near the end of August or first of Sept. Beginning approximately one month after planting, and continuing to April 1, the plants are subjected to light from 2:00 a.m. to 6:00 a.m. daily. A lighting system which has proved highly effective consists of 135 watt bulbs spaced every 10 feet, and hung approximately 7 feet above the ground. The bulbs are positioned in rows that are spaced 12 feet apart.

By effectively increasing the day length by means of artificial lighting, flowering can be initiated in a much shorter time. Within approximately six (6) weeks the first flower appears, and saleable stems are ready from mid-November to mid-December, depending upon the variety. In many instances, flowering is essentially continuous until June when the stems are too short to sell as cuts without heavy shading and some method of cooling. Without shading and cooling to prolong commercial stem production, it is common practice to dig up an divide the plants. The divided plants are then stuck in late August or early September as described, and the cycle repeated. It has also been noted that the increased light regimen has resulted in longer stems, a very desirabel quality.

Diana was originated by the inventor Erwin Mojonnier in a controlled breeding program in Encinitas, Calif. in 1988. The new cultivar was produced from the selfing of a cultivar designated as L4, a tall plant having flowers with a generally red background, grayed-purple streaking on both the upper and lower petals, and a yellow patch or area on each of the upper petals.

Diana was discovered and selected as one flowering plant within the progeny of the stated parentage by Erwin Mojonnier in May 1988 in a controlled environment in Encinitas, Calif.

The first act of asexual reproduction of Diana was accomplished when vegetative cuttings were taken from the initial selection in August 1988 in a controlled environment in Encinitas, Calif. by Erwin Mojonnier. Horticultural examination of selected units initiated in 1989 has demonstrated that the combination of characteristics as herein disclosed for Diana are firmly fixed and retained through successive generations of asexual reproduction.

Diana has not been observed under all possible environmental conditions. The phenotype may vary significantly with variations in environment such as temperature, light intensity and day length. The following observations, measurements and comparisons describe plants grown in Encinitas, Calif. under greenhouse conditions which approximate those generally used in commercial practice.

The following traits have been repeatedly observed and are determined to be basic characteristics of Diana, which in combination distinguish this Alstroemeria as a new and distinct cultivar:

1. Low maintenance, with few non-flowering stems produced per plant.

2. Diana is responsive to increased light for initiating flowering. By effectively increasing day length by artificial light in optimum amounts, the first flower appears approximately six weeks after rhizome planting, and saleable stems in full flower are ready by early December. Thus, winter production can begin relatively early and, through photoperiodic control, continue throughout the winter period. Production can therefore be effectively staggered continuously through winter periods of low natural light.

3. Diana is easily propagated from rhizomes.

4. The main or background flower color is pink, with dark red cheeks. Streaking appears most heavily in the upper petals, but appears on the lower petal as well. The lower portion of each upper petal shows prominent yellow areas.

5. Diana possesses good post-harvest color retention.

The accompanying color photographic drawing shows typical inflorescence and foliage characteristics of Diana, with colors being as nearly true as possible with illustration of this type. The photograph comprises an enlarged close-up view of an open flower of Diana, with the flower parts and color being clearly illustrated.

In the following description, color references are made to The Royal Horticultural Society Color Chart (R.H.S.). The color values were determined between 9:45 and 10:30 a.m. on Apr. 26, 1990 under 2000 foot candles of light intensity at Encinitas, Calif.

Classification: Alstroemeria cv. Diana.
Commercial: Alstroemeria.

Plant

Form: Cut flower.
Height: Tall; approximately 129 cm. at time of harvest.
Propagation: From rhizomes.
Growth habit: Excellent.
Foliage:
- *Quantity.*—Approximately 28 leaves per stem.
- *Size of leaf.*—Approximately 15 cm.×3.5 cm.
- *Shape of leaf.*—Lanceolate.
- *Color.*—Upper side, yellow-green 147A; under side, green 138A.

Rhizomes:
- *Color.*—White, 155B.
- *Size.*—1 cm.×1 cm. at growing tip.

INFLORESCENCE

Bud:
- *Form.*—Indeterminate.
- *Diameter.*—1.4 cm.
- *Length.*—4.0 cm.
- *Calyx.*—4.6 mm.
- *Peduncle.*—Approximately 4.2 cm. in length.
- *Color.*—Green, 138B.

Flower:
- *Size.*—Approximately 4.7 cm. in total diameter.
- *Borne.*—5 flowers per umbel.
- *Blooming habit.*—Begins flowering in early December, approximately three months after planting of rhizomes cuttings.
- *Shape.*—Asymmetrical.
- *Color.*—Generally, Diana has a dark red cheek on a pink background. There is grayed-purple streaking on upper and lower petals, with streaking on upper petals being more prominent. The upper petals have yellow patches toward the base, and a prominent yellow throat. The sepals possess green tips which can be observed on the upper and under surfaces. Upper surface: Background, red-purple 73B. Cheek, red-purple 57B. Under surface: Background, red-purple 73B. Cheek, red-purple 57B. Other notations: Streaks: Grayed-purple b 187A. Yellow throat: Yellow 4A. Green tip: Green 143A. White area around green tip: White 155C.
- *Peduncle.*—Length, 9.3 cm.; color, green 138A.
- *Lasting quality.*—Cut flowers last approximately 14 days after harvest.

REPRODUCTIVE ORGANS

Stamens: Number, 6.
Anthers: Color, grey-brown, 199C.
Filaments: Color, red-purple b 73B.
Pistils: Number, 1; color, red-purple 73B.
Stigma: Color, red-purple 73B.

I claim:

1. A new and distinct cultivar of Alstroemeria plant named Diana, as illustrated and described.

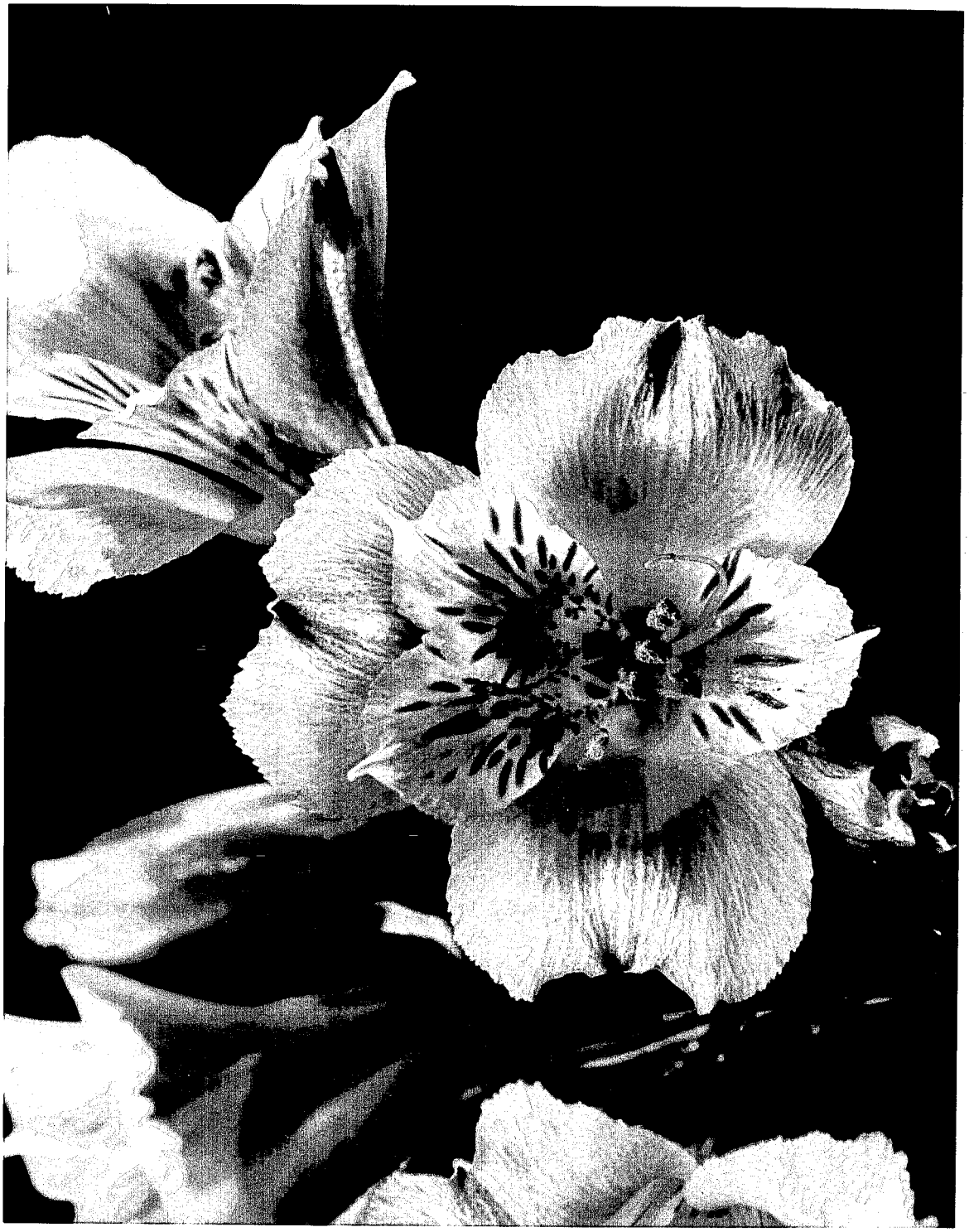

* * * * *